United States Patent
Lin et al.

(10) Patent No.: US 10,807,440 B2
(45) Date of Patent: Oct. 20, 2020

(54) DUAL-PASSAGE AIR QUALITY DETECTION DEVICE

(71) Applicant: Xiamen Maxmac Air Technology Co., Ltd., Xiamen, Fujian (CN)

(72) Inventors: Yangxin Lin, Xiamen (CN); Changping Lin, Xiamen (CN); Minsong Lin, Xiamen (CN)

(73) Assignee: MAXMAC SHANGHAI AUTOMOTIVE ELECTRONIC CO., LTD., Shanghai (CN)

( * ) Notice: Subject to any disclaimer, the term of this patent is extended or adjusted under 35 U.S.C. 154(b) by 349 days.

(21) Appl. No.: 15/871,088

(22) Filed: Jan. 15, 2018

(65) Prior Publication Data
US 2019/0217681 A1    Jul. 18, 2019

(51) Int. Cl.
*B60H 1/00* (2006.01)
*G01N 33/00* (2006.01)

(52) U.S. Cl.
CPC ......... *B60H 1/00792* (2013.01); *B60H 1/008* (2013.01); *B60H 1/00521* (2013.01); *B60H 1/00564* (2013.01); *G01N 33/0036* (2013.01)

(58) Field of Classification Search
CPC ............ B60H 1/00792; B60H 1/00521; B60H 1/00564
USPC .......................................................... 73/31.01
See application file for complete search history.

(56) References Cited

U.S. PATENT DOCUMENTS

| 5,084,629 A | * | 1/1992 | Petralli | G01N 21/53 250/573 |
| 2019/0195766 A1 | * | 6/2019 | Ryu | G01N 15/06 |

* cited by examiner

*Primary Examiner* — Tarun Sinha
(74) *Attorney, Agent, or Firm* — Leong C. Lei

(57) ABSTRACT

A dual-passage air quality detection device includes a housing, an air quality detection module, a fan, and a main control PCB (printed circuit board). The air quality detection module includes two passages, two laser modules and two photodiodes therein. The fan includes two fans. One of the passages is communicated with the inside of the vehicle, and the other of the passages is communicated with the outside of the vehicle to form two independent air passages for detection. Each of the passages corresponds to one fan for independent sampling, not affecting each other.

11 Claims, 13 Drawing Sheets

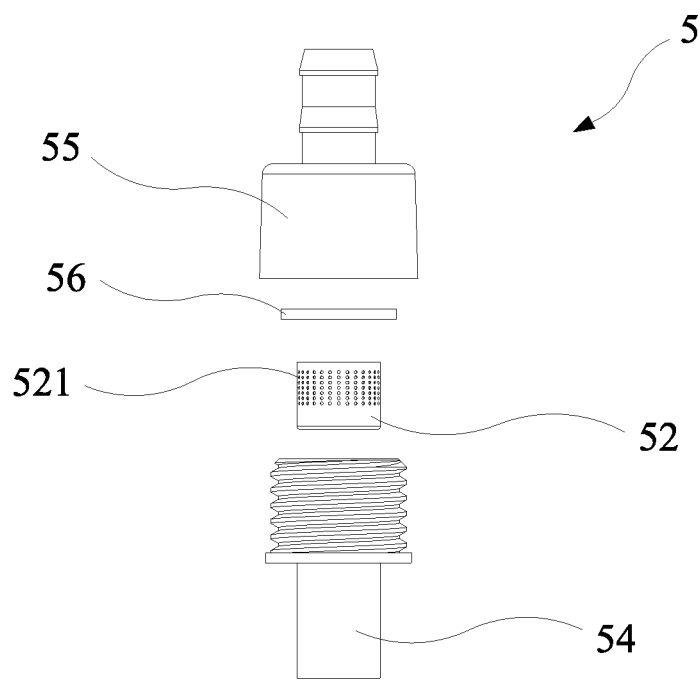
F I G. 6
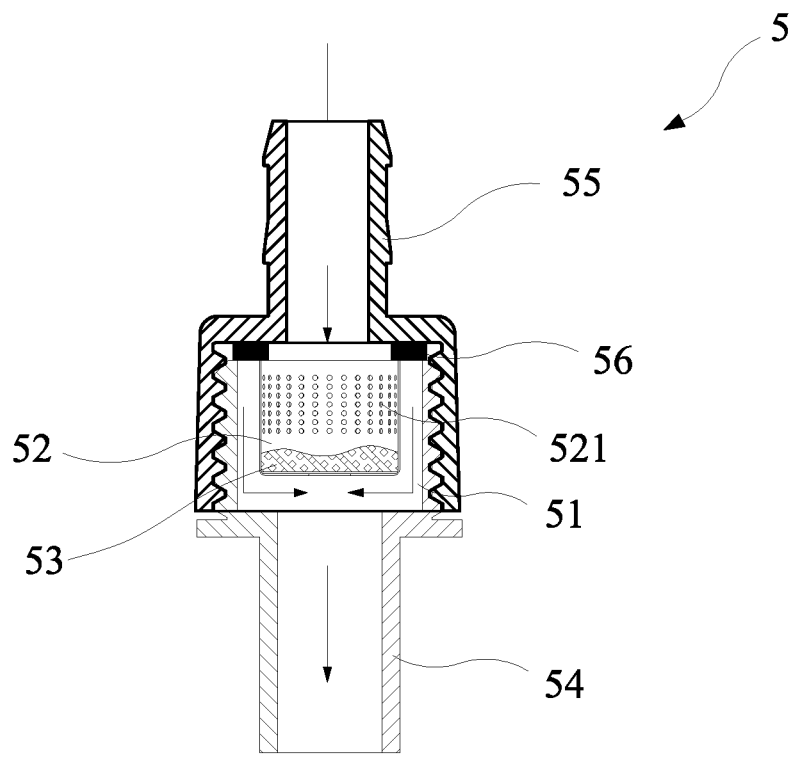
F I G. 7

DUAL-PASSAGE AIR QUALITY DETECTION DEVICE

BACKGROUND OF THE INVENTION

1. Field of the Invention

The present invention relates to an air quality detection device, and more particularly to a vehicle-mounted dual-passage air quality detection device.

2. Description of the Prior Art

In the prior art, a conventional vehicle-mounted air purifier detects the air quality inside the vehicle by using a PM2.5 air sensor, which is an air purifier used in the vehicle. The air purifier can only detect the air quality inside the vehicle, but it cannot detect the air quality outside the vehicle.

In order to solve the aforesaid problem, Chinese Patent Application No. 201720077961.1 is a prior application filed by the applicant of the present invention, which discloses a dual-passage air quality detection device comprising a housing, a first laser module, a first silicon photodiode, a second laser module, a second silicon photodiode, a PCB assembly, and a fan. The housing is formed with a first intake passage and a second intake passage. The PCB assembly is mounted in the housing. The first laser module and the first silicon photodiode are mounted on the PCB assembly, and electrically connected to the PCB assembly, respectively. The transmitting end of the first laser module is located in the first intake passage. The first silicon photodiode is located in the first intake passage. The second laser module and the second silicon photodiode are mounted on the PCB assembly, and electrically connected to the PCB assembly, respectively. The transmitting end of the second laser module is located in the second intake passage. The second silicon photodiode is located in the second intake passage.

The fan is installed in the housing. An intake end of the fan is connected with the air outlet ends of the first intake passage and the second intake passage. An exhaust end of the fan is communicated with the outside air. For detecting the air quality, one intake passage is communicated with the inside of the vehicle, and the other intake passage is communicated with the outside of the vehicle to form two independent air passages for detection. The air is exhausted through the fan. The PCB assembly is provided with the laser modules. The laser light passes through the air passage. The scattered light of dust particles in the air passage is fed back to the silicone photodiode. The potential of the silicone photodiode changes by circuit data processing to obtain the PM2.5 value.

Although the prior patent has obvious advantages over the conventional vehicle-mounted air purifier, the following deficiencies still exist:

1. The dual-passage air quality detection module uses a single fan to exhaust two passages. When this structure is used to sample the air outside the vehicle, the airflow generated by the air conditioner may affect the detection accuracy of the module. It cannot take into account the detection stability of the two passages.

2. Before the laser module is used, it is necessary to check whether its laser intensity meets the requirement so as to ensure the normal operation of the air quality detection module. The first laser module and the second laser module of the prior patent are arranged in parallel at the same side of the housing. The distance between the two laser modules is small. When the laser intensity of the two laser modules is calibrated, it is easy to interfere with each other. It is not beneficial for the calibration of the laser intensity of the laser module. The two laser modules are arranged in parallel and the vertical space occupied is large, which is not beneficial for the miniaturization of the product. This structure is designed for placement of a single fan, not for placement of two fans.

3. The conventional fan is provided with lead terminals which are assembled manually, not meeting the requirement of the automated assembly.

4. As the fan of the prior patent is not provided with a noise reduction mechanism. When the fan is used, it will be disturbed by the airflow to generate noises and affect the product experience.

5. As the sampling opening of the air quality inspection module is usually set in a central control device of a vehicle. The central control device has an engine. The engine generates heat while the vehicle is running, so that the temperature of the surrounding air rises. When sampling, the air enters the engine from the sampling tube to be heated and then enters a colder tube (especially when the air conditioner of the vehicle is turned on), and the air is cooled to form condensate water, such that the detected air quality and the actual air quality have a greater difference, affecting the accuracy of detection.

Accordingly, the inventor of the present invention has devoted himself based on his many years of practical experiences to solve these problems.

SUMMARY OF THE INVENTION

The primary object of the present invention is to provide a dual-passage air quality detection device with has high detection accuracy and stability. The overall structure is compact. It is convenient to detect the laser intensity.

Another object of the present invention is to provide a dual-passage air quality detection device which can achieve the automated assembly.

A further object of the present invention is to provide a dual-passage air quality detection device which can lower the noise.

In order to achieve the aforesaid object, the dual-passage air quality detection device of the present invention comprises a housing. An air quality detection module, a fan and a main control PCB (printed circuit board) connected with the air quality detection module and the fan are provided in the housing. The air quality detection module is formed with a first passage and a second passage therein. The first passage and the second passage have sampling openings and air outlets, respectively. The fan includes a first fan and a second fan corresponding to the first passage and the second passage. An air inlet end of the first fan is connected with the air outlet of the first passage. An air inlet end of the second fan is connected with the air outlet of the second passage. Air outlet ends of the first and second fans are communicated with external air. The air quality detection module includes a first laser module and a second laser module corresponding to the first passage and the second passage. Transmitting ends of the first and two laser modules are arranged in a V-shaped configuration. The transmitting end of the first laser module is located in the first passage. A first photodiode is provided in the first passage, facing the transmitting end of the first laser module. The transmitting end of the second laser module is located in the second passage. A second photodiode is provided in the second passage, facing the transmitting end of the second laser module. The first and second laser modules and the first and second photodiodes are electrically connected to a circuit board of the air quality detection module. The circuit board is electrically connected to the main control PCB.

Preferably, the air quality detection module has a rectangular main body and the circuit board. The first passage, the second passage, the first and second laser modules and the first and second photodiodes are disposed in the main body.

Preferably, the sampling openings of the first passage and the second passage are disposed at a same side of the main body. The first passage and the second passage are respectively L-shaped or J-shaped. The transmitting ends of the first laser module and the second laser module face respective corners of the L-shaped or J-shaped first and second passages.

Preferably, the sampling openings of the first passage and the second passage are disposed at two sides of the main body, respectively. The first passage and the second passage are respectively Z-shaped. The transmitting ends of the first laser module and the second laser module face respective corners of the Z-shaped first and second passages far away from the sampling openings.

Preferably, each of the sampling openings of the first passage and the second passage is connected to a sampling tube through a connector. One end of the connector is connected to the sampling openings. Another end of the connector is connected to the sampling tube. The connector has an accommodation chamber therein. The accommodation chamber is provided with a filter cartridge. The filter cartridge is provided with a plurality of air holes for air circulation. The accommodation chamber is provided with a water tank under the air holes for storing condensate water.

Preferably, the connector includes a plug connected with the sampling openings and a tube plug connected with the sampling tube. The plug is connected to the tube plug. The junction of the plug and the tube plug is formed with the accommodation chamber. The filter cartridge is disposed in the accommodation chamber. One end of the filter cartridge, connected with the tube plug, is formed with the air holes. The filter cartridge is directly formed with the water tank below the air holes. A sealing gasket is provided in the accommodation chamber at the end where the filter cartridge is connected to the tube plug.

Alternatively, the connector includes a plug connected with the sampling openings and a tube plug connected with the sampling tube. The plug is connected to the tube plug. One end of the tube plug is connected to the sampling pipe. Another end of the tube plug is connected to the plug. The accommodation chamber is disposed between the two ends of the tube plug. The end of the tube plug, connected with the plug, extends into the accommodation chamber and is formed with a protruding wall so that the accommodation chamber is formed with the water tank around the protruding wall. The filter cartridge has an arc shape and is disposed between the protruding wall of the tube plug and the plug. A sealing gasket is provided between the filter cartridge and the protruding wall of the tube plug.

Preferably, the first fan and the second fan each include a fan casing. The fan casing is provided with a rotor and a wind wheel therein. The fan casings of the first and second fans are connected together by a connecting plate. The connecting plate is provided with a thimble connector thereon. The rotor is provided with a plurality of leads. Each of the leads is connected to the thimble connector. The thimble connector is provided with a plurality of thimbles thereon. The main control PCB is provided with a plurality of conductive contacts corresponding to the thimbles. The circuit board of the air quality detection module is provided with a plurality of metal contacts. The main control PCB is provided with a plurality of pins corresponding to the metal contacts.

Preferably, a fan sealing cover is provided to mate with a top of the fan casing. The fan sealing cover has connection holes corresponding in position to the first fan and the second fan respectively. A fan cushion is provided at a bottom of the fan casing.

Preferably, each of the air outlet ends of the first fan and the second fan is provided with a noise reduction connector having a smooth an inner wall. The noise reduction connector is tapered outwardly from the air outlet ends of the first fan and the second fan.

Preferably, the housing includes an upper casing, a middle casing, and a lower casing. The upper casing is mated with an upper portion of the middle casing. The lower casing is mated with a lower portion of the middle casing. The middle casing is partitioned into an upper chamber and a lower chamber by a partition. The air quality detection module is disposed in the upper chamber of the middle casing. The first fan and the second fan are disposed in the lower chamber of the middle casing. The main control PCB is disposed in the upper chamber or the lower chamber of the middle casing. The partition has two through holes corresponding to the first passage and the second passage. The partition further has perforations for the main control PCB to connect with the first and second fans or the air quality detection module.

Compared to the prior art, the dual-passage air quality detection device of the present invention is provided with the two fans. The two fans respectively sample the air inside and outside the vehicle and do not influence each other so as to effectively reduce the influence on the sampling airflow of the module and to ensure the accuracy of detection when the air conditioner is turned on. Moreover, the transmitting ends of the two laser modules of the present invention are arranged in a V-shaped configuration, which effectively reduces the longitudinal length of the air detection module. The V-shaped configuration allows the transmitting ends of the two laser modules to have a large spacing. When laser calibrators are used to check the laser intensity of the laser modules, they will not interfere with each other for easy detection. The two laser modules are designed in a V-shaped configuration so that the two air outlet of the first passage and the second passage have a large spacing. The present invention may be provided with two suction fans to effectively reduce the influence of the sampling airflow on the environment and the sampling performance of the fans, improving the accuracy of the air quality detection inside and outside the vehicle.

Furthermore, each of the sampling openings of the first passage and the second passage is connected with the sampling tube through the connector. The filter cartridge is disposed in the connector for removing condensate water in the sampling tube. Particularly, when the air outside the vehicle is sampled, the condensate water formed in the sampling tube after the engine is heated and then cooled can be effectively removed to ensure the accuracy of detection.

Furthermore, the present invention meets the requirements of the fully automated assembly. The thimbles of the thimble connector of the fan are connected with the conductive contacts of the main control PCB, and the metal contacts of the circuit board of the air quality detection module are connected with the pins of the main control PCB, thereby improving the production and assembly efficiency greatly and facilitating inspection and maintenance.

Furthermore, the air outlet ends of the first fan and the second fan of the present invention are connected with the noise reduction connectors to provide great suction and to lower the noise, which improves the user's experience. In addition, the upper portion of the fan casing is covered with the fan sealing cover, and the upper portion of the fan casing is provided with the fan cushion to effectively reduce the noise when the first fan and the fan are running.

BRIEF DESCRIPTION OF THE DRAWINGS

FIG. 6 is an exploded view of a first embodiment of the connector provided at the sampling opening of the present invention;

FIG. 7 is a sectional view showing the operation of the first embodiment of the connector provided at the sampling opening of the present invention;

DETAILED DESCRIPTION OF THE PREFERRED EMBODIMENTS

Embodiments of the present invention will now be described, by way of example only, with reference to the accompanying drawings.

Figure 1:
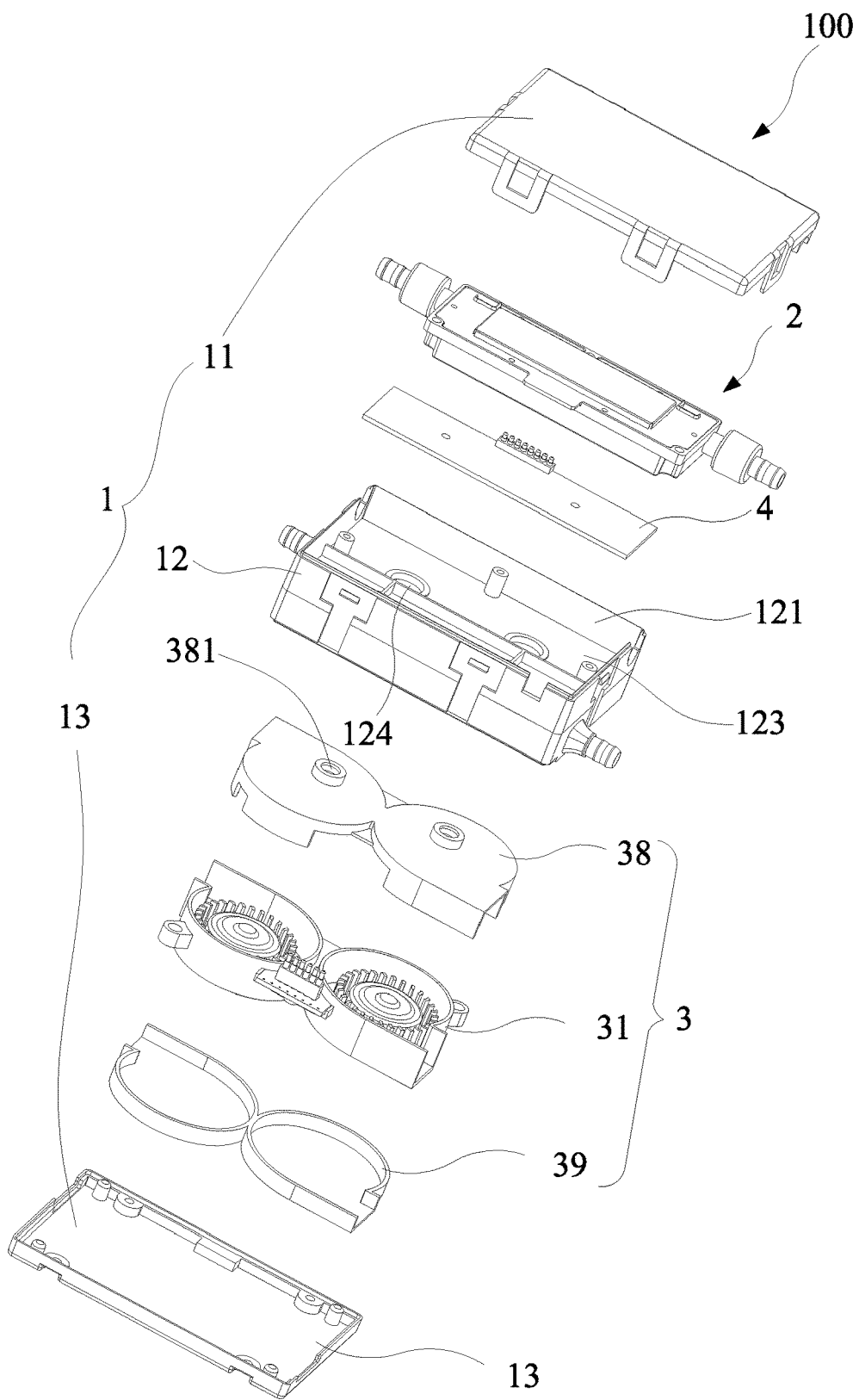
FIG. 1 is an exploded view of the present invention.

As shown in FIG. 1, the present invention discloses a dual-passage air quality detection device 100. The dual-passage air quality detection device 100 comprises a housing 1. An air quality detection module 2, a fan 3, and a main control PCB (printed circuit board) 4 connected with the air quality detection module 2 and the fan 3 are provided in the housing 1.

As shown in FIG. 1, the housing 1 includes an upper casing 11, a middle casing 12, and a lower casing 13. The upper casing 11 is mated with an upper portion of the middle casing 12. The lower casing 13 is mated with a lower portion of the middle casing 12. The middle casing 12 is partitioned into an upper chamber 121 and a lower chamber 122 by a partition 123. The air quality detection module 2 is disposed in the upper chamber 121 of the middle casing 12. The fan 3 is disposed in the lower chamber 122 of the middle casing 12. The main control PCB 4 is disposed in the upper chamber 121 or the lower chamber 122 of the middle casing 12. The partition 123 has two through holes 124. The partition 123 further has a perforation for the main control PCB 4 to connect with the fan 3 or the air quality detection module 2.

Figure 2:
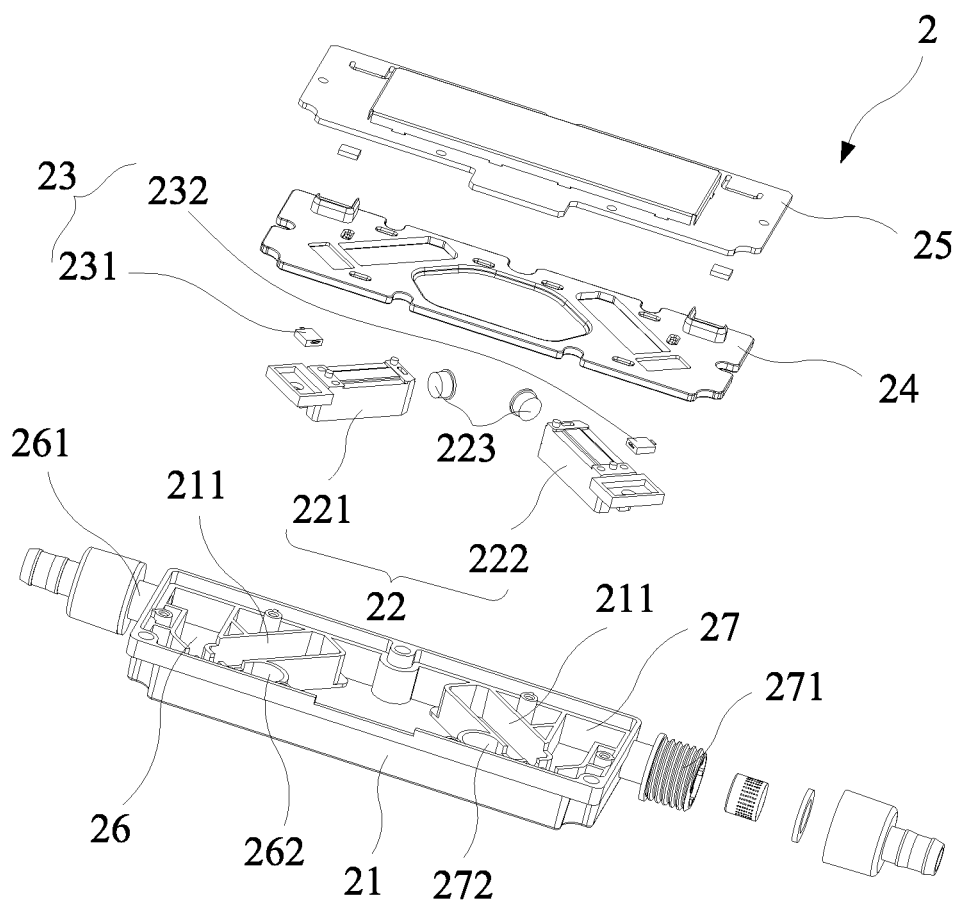
FIG. 2 is an exploded view of the air quality detection module of the present invention.

As shown in FIG. 2, the air quality detection module 2 has a rectangular main body 21, two laser modules 22, two photodiodes 23, a gasket 24, and a circuit board 25. The two laser modules 22 and the two photodiodes 23 are disposed in the main body 21. The circuit board 25 covers the top of the main body 21. The gasket 24 is disposed in the main body 21 and located beneath the circuit board 25. The main body 21 has a first passage 26 and a second passage 27 therein. The first passage 26 and the second passage 27 have sampling openings 261, 271 and air outlets 262, 272, respectively. The two laser modules 22 are a first laser module 221 and a second laser module 222. The main body 21 has mounting troughs 211 for mounting the first laser module 221 and the second laser module 222. One end of each of the first laser module 221 and the second laser module 222 is a transmitting end, and the other end is provided with a battery 223 for supplying power to the first laser module 221 and the second laser module 222. The first laser module 221 and the second laser module 222 are disposed corresponding to the first passage 26 and the second passage 27. The transmitting end of the first laser module 221 is located in the first passage 26. The transmitting end of the second laser module 222 is located in the second passage 27. The transmitting ends of the two laser modules 221, 222 are arranged in a V-shaped configuration. The two photodiodes 23 include a first photodiode 231 and a second photodiode 232. The first photodiode 231 is disposed in the first passage 26, facing the transmitting end of the first laser module 221. The second photodiode 232 is disposed in the second passage 27, facing the transmitting end of the second laser module 222. The two laser modules 22 and the two photodiodes 23 are electrically connected to the circuit board 25. One side of the circuit board 25 is provided with a plurality of metal contacts 251 for connecting with the main control PCB 4.

Figure 3:
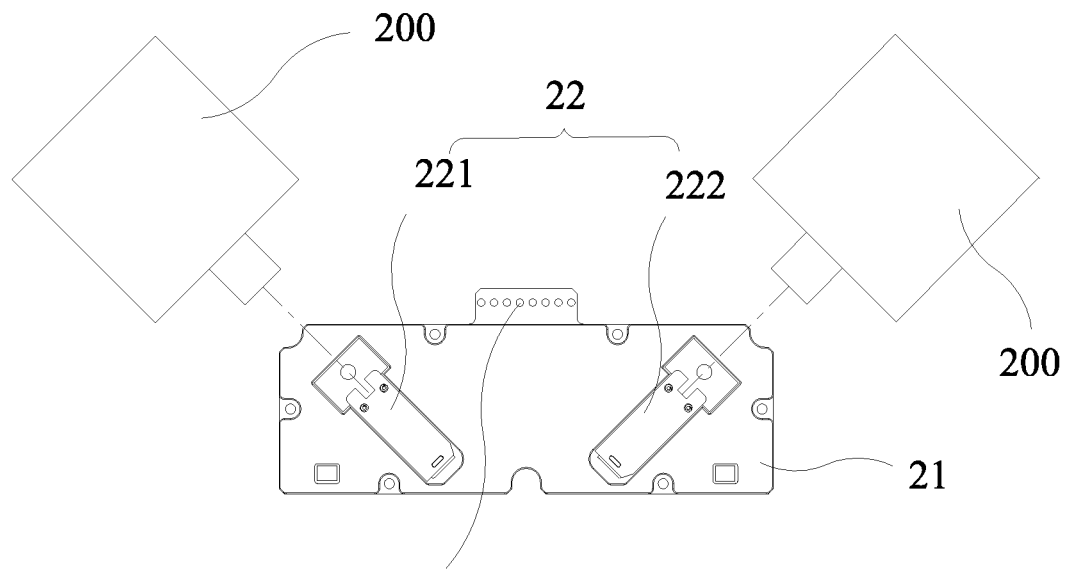
FIG. 3 is a schematic view of the present invention, showing that the laser calibrators are used to check the laser intensity of the laser module.

As shown in FIG. 3, after the first laser module 221 and the second laser module 222 are mounted and before use, the laser intensity of the first laser module 221 and the second laser module 222 needs to be checked to ensure the accuracy of the air quality detection. For detection, the first laser module 221 and the second laser module 222 with the batteries 223 are mounted in the first passage 26 and the second passage 27 of the main body 21 and arranged in a V-shaped configuration. Two laser calibrators 200 are respectively placed in front of the transmitting ends of the first laser module 221 and the second laser module 222 to check the laser intensity of the first laser module 221 and the second laser module 222. Of course, the first laser module 221 and the second laser module 222 may be checked by one laser calibrator 200.

Figure 4:
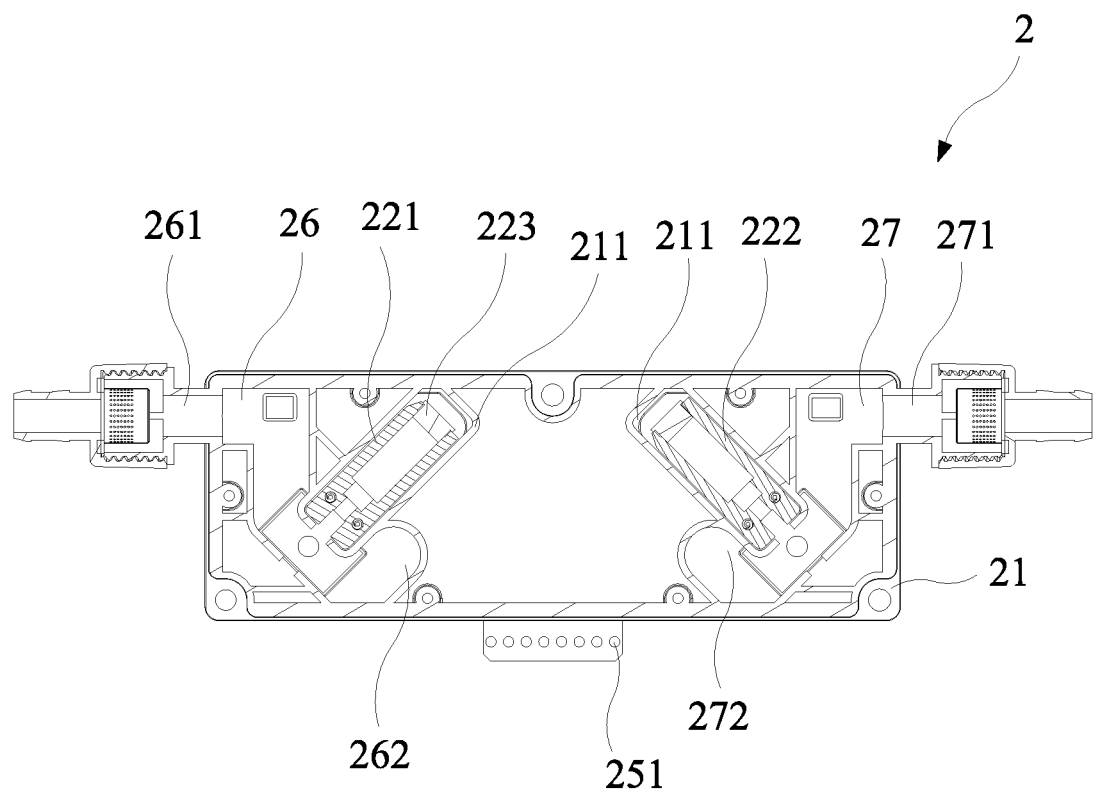
FIG. 4 is a sectional view of a first embodiment of the air quality detection module of the present invention.

FIG. 4 illustrates a first embodiment of the air quality detection module 2 of the present invention. Wherein, the sampling openings 261, 271 of the first passage 26 and the second passage 27 are disposed at two sides of the main body 21, respectively. The first passage 26 and the second passage 27 are respectively Z-shaped. The transmitting ends of the first laser module 221 and the second laser module 222 face the respective corners of the Z-shaped first and second passages far away from the sampling openings 261, 271, respectively.

Figure 5:
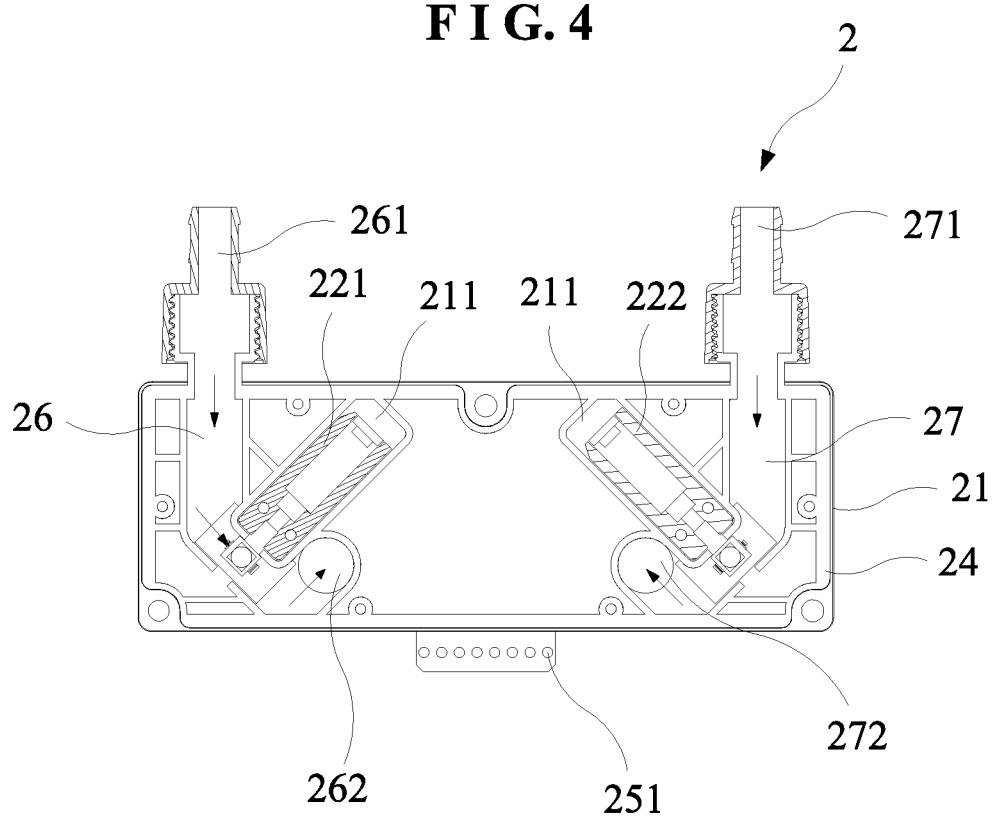
FIG. 5 is a sectional view of a second embodiment of the air quality detection module of the present invention.

FIG. 5 illustrates a second embodiment of the air quality detection module 2 of the present invention. Wherein, the sampling openings 261, 271 of the first passage 26 and the second passage 27 are disposed at the same side of the main body 21. The first passage 26 and the second passage 27 are respectively L-shaped or J-shaped. The transmitting ends of the first laser module 221 and the second laser module 222 face the respective corners of the L-shaped or J-shaped first and second passages.

No matter the first passage 26 and the second passage 27 are configured as shown in FIG. 4 or FIG. 5, the first laser module 221 and the second laser module 222 are disposed in the main body 21 in a V-shaped configuration so that the longitudinal length of the air quality detection module 2 can be reduced effectively. The V-shaped configuration allows the transmitting ends of the two laser modules 22 to have a large spacing. When the laser calibrators 200 are used to check the laser intensity of the laser modules 22, they will not interfere with each other for easy detection. The two laser modules 22 are designed in a V-shaped configuration so that the two air outlets 262, 272 of the first passage 26 and the second passage 27 have a large spacing. The present invention may be provided with two suction fans 3 to effectively reduce the influence of the sampling airflow on the environment and the sampling performance of the fans, improving the accuracy of the air quality detection inside and outside the vehicle.

Figure 17:
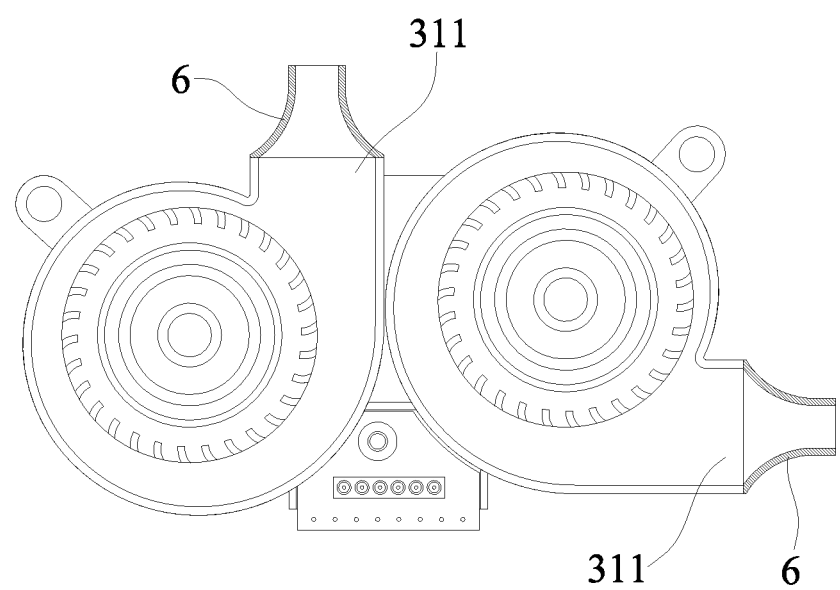
FIG. 17 is a top view of a third embodiment of the fan of the present invention.

As shown in FIG. 2 in conjunction with FIG. 6 to FIG. 9, each of the sampling openings 261, 271 of the first passage 26 and the second passage 27 is connected to a sampling tube 300 (as shown in FIG. 17) through a connector 5. One end of the connector 5 is connected to the sampling openings 261, 271. Another end of the connector 5 is connected to the sampling tube 300. The connector 5 has an accommodation chamber 51 therein. The accommodation chamber 51 is provided with a filter cartridge 52. The filter cartridge 52 is provided with a plurality of air holes 521 for air circulation. The accommodation chamber 51 is provided with a water tank 53 under the air holes 521 for storing condensate water. The filter cartridge 52 is disposed in the connector 5 for removing condensate water in the sampling tube 300. Particularly, when the air outside the vehicle is sampled, the condensate water formed in the sampling tube 300 after the engine is heated and then cooled can be effectively removed so that the air entering the air quality detection module 2 will not be influenced by the condensate water so as to ensure the accuracy of detection. When the present invention is sampled, the air enters the sampling tube 300. When the air passes through a hotter section, the air will be heated. When the heated air enters the colder tube, it will form condensate water. The air with condensate water enters a tube plug 55 of the connector 5 and then passes through the filter cartridge 52. The gas in the air enters the accommodation chamber 51 through the air holes 521 of the filter cartridge 52 and enters the plug, finally enters the first passage 26 and the second passage 27. The condensate water in the air enters the tube plug 55 and is separated by the filter cartridge 52 to be stored in the water tank 53 of the connector 5.

FIG. 6 and FIG. 7 illustrate a first embodiment of the connector 5 of the present invention. As shown in the figures, in this embodiment, the connector 5 includes a plug 54 connected with the sampling openings 261, 271 and a tube plug 55 connected with the sampling tube 300. The plug 54 is connected to the tube plug 55. The connection may be implemented by thread, snap-fit, mortise in cooperation with tenon, or other ways. The junction of the plug 54 and the tube plug 55 is formed with the accommodation chamber 51. The filter cartridge 52 is disposed in the accommodation chamber 51. An upper portion of one end of the filter cartridge 52, connected with the tube plug 55, is formed with the air holes 521. The filter cartridge 52 is directly formed with the water tank 53 below the air holes 521. A sealing gasket 56 is provided in the accommodation chamber 51 at the end where the filter cartridge 52 is connected to the tube plug 55.

Figure 8:
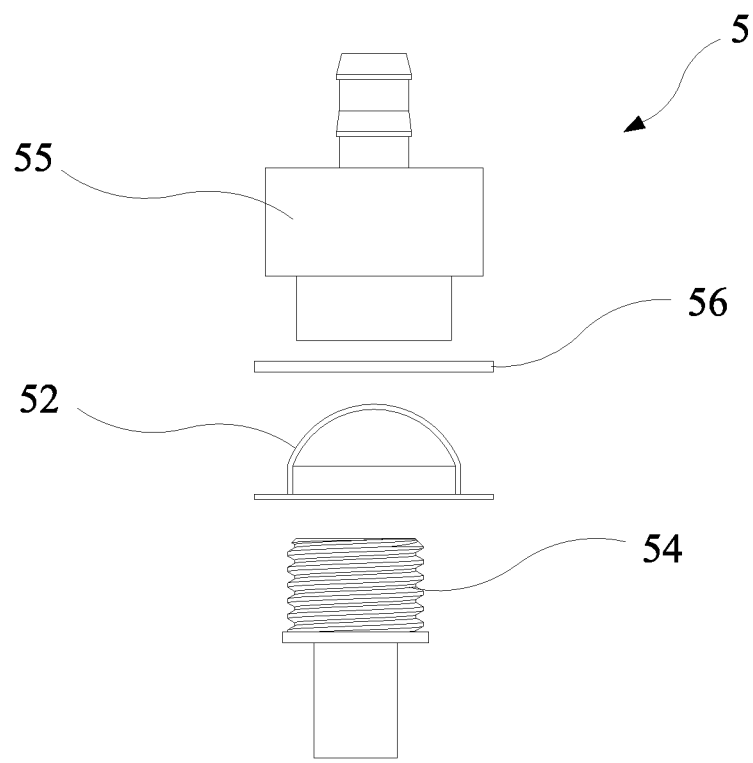
FIG. 8 is an exploded view of a second embodiment of the connector provided at the sampling opening of the present invention.
Figure 9:
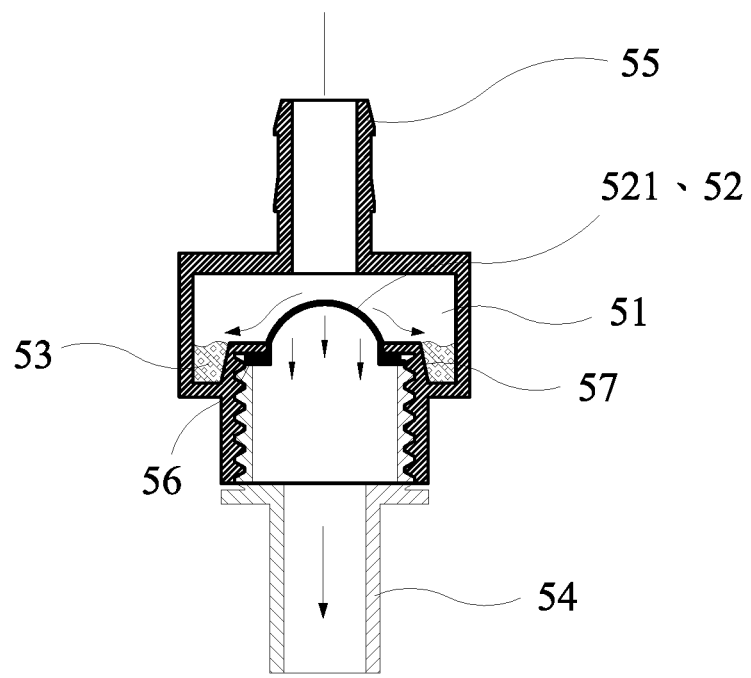
FIG. 9 is a sectional view showing the operation of the second embodiment of the connector provided at the sampling opening of the present invention.

FIG. 8 and FIG. 9 illustrate a second embodiment of the connector 5 of the present invention. As shown in FIG. 8, in this embodiment, each connector 5 includes a plug 54 connected with the sampling openings 261, 271 and a tube plug 55 connected with the sampling tube 300. The plug 54 is connected to the tube plug 55. One end of the tube plug 55 is connected to the sampling pipe 300, and another end of the tube plug 55 is connected to the plug 54. The accommodation chamber 51 is disposed between the two ends of the tube plug 55. The end of the tube plug 55, connected with the plug 54, extends into the accommodation chamber 51 and is formed with a protruding wall 57. The accommodation chamber 51 is formed with the water tank 53 around the protruding wall 57. The filter cartridge 52 has an arc shape and is disposed between the protruding wall 57 of the tube plug 55 and the plug 54. The plurality of the air holes 521 are directly formed on the arc-shaped filter cartridge 52. A sealing gasket 56 is provided between the filter cartridge 52 and the protruding wall 57 of the tube plug 55.

As shown in FIG. 1 in conjunction with FIG. 10 to FIG. 14, the fan 3 includes a first fan 3A and a second fan 3B. The first fan 3A and the second fan 3B are arranged corresponding to the first passage 26 and the second passage 27 of the air quality detection module 2. The first fan 3A and the second fan 3B are disposed in two fan casings 31, respectively. Each fan casing 31 has an air outlet end 311. The first fan 3A and the second fan 3B each include a rotor 32, a magnetic ring 33, a wind wheel 34, a bearing 35, and a snap ring 36. The two fan casings 31 are connected together by a connecting plate 37. The connecting plate 37 is provided with a thimble connector 371 thereon. A fan sealing cover 38 is provided on the top of the two connected fan casings 31. The fan sealing cover 38 has connection holes 381 respectively corresponding in position to the first fan 3A and the second fan 3B. The connection holes 381 serve as air inlets of the first fan 3A and the second fan 3B. The two connection holes 381 are communicated with the air outlets 262, 272 of the first passage 26 and the second passage 27. A fan cushion 39 is provided at the bottom of each fan casing 31.

Figure 10:
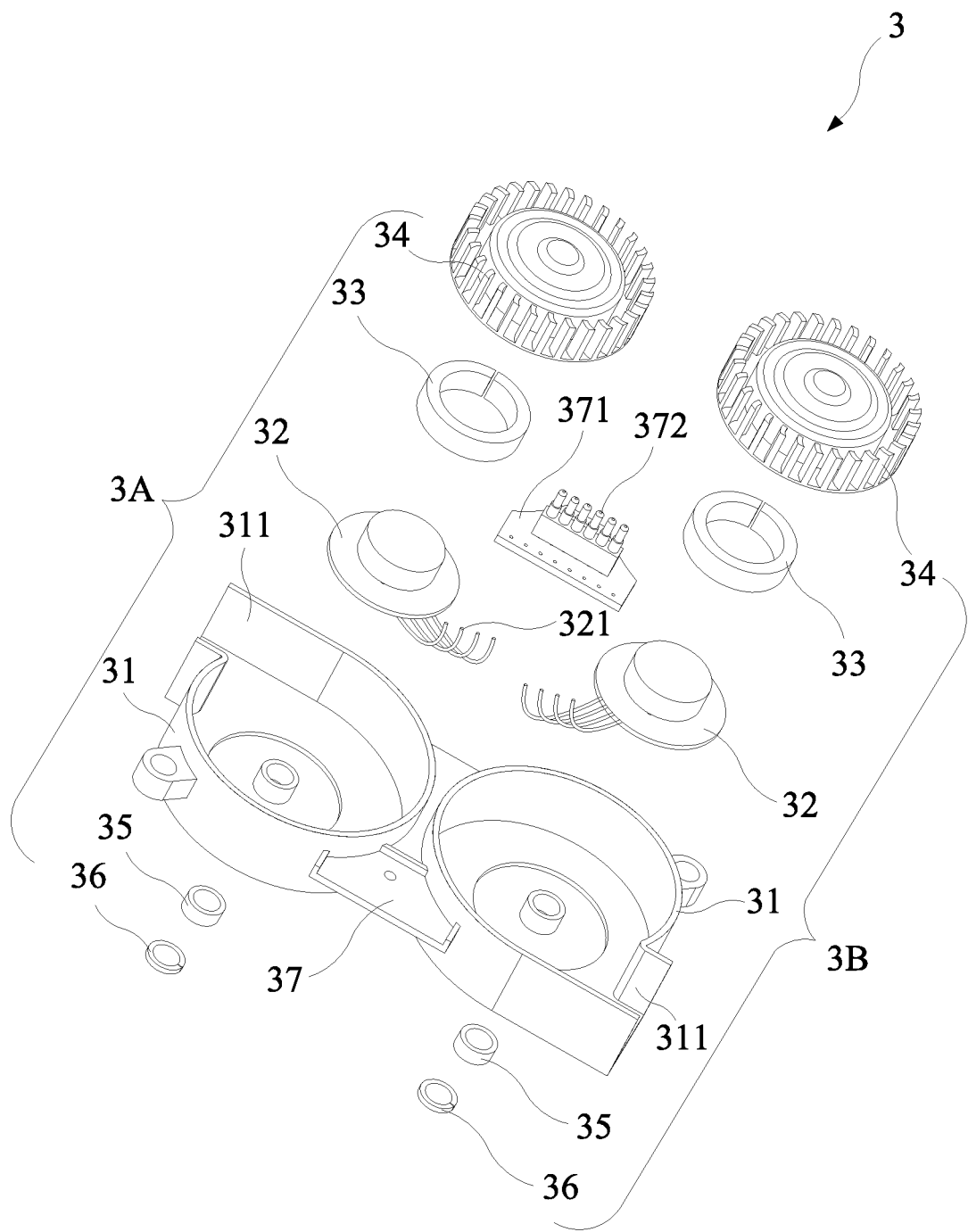
FIG. 10 is an exploded view of the fan of the present invention.
Figure 12:
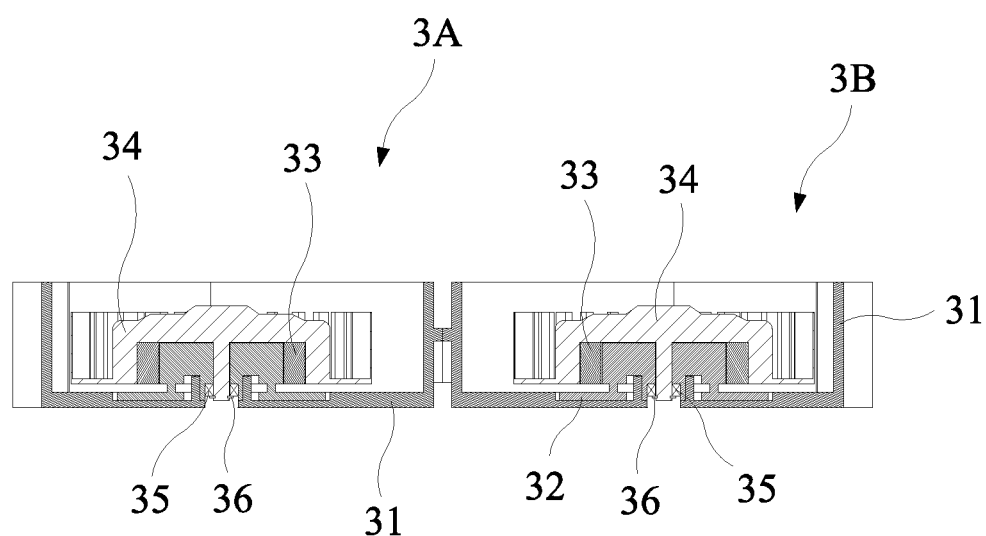
FIG. 12 is a sectional view of FIG. 11.

As shown in FIG. 10 and FIG. 12, the rotor 32 and the fan casing 31 are fixed together. The magnetic ring 33 is connected to the wind wheel 34, and is rotatably sleeved on the rotor 32. The wind wheel 34 is rotatably connected to the fan casing 31 through the bearing 35 and the snap ring 36. The rotor 32 is provided with a plurality of leads 321. Each of the leads 321 is connected to the thimble connector 371. The thimble connector 371 is provided with a plurality of thimbles 372 thereon.

Figure 11:
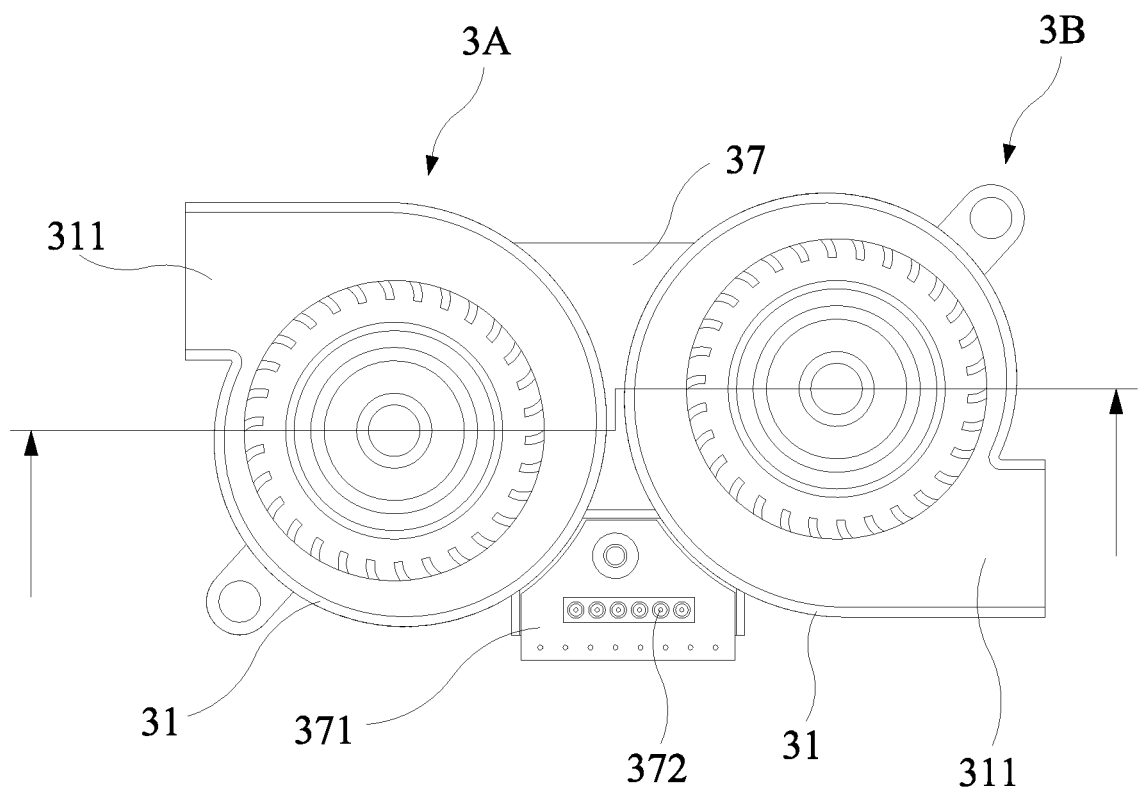
FIG. 11 is a top view of a first embodiment of the fan of the present invention.
Figure 13:
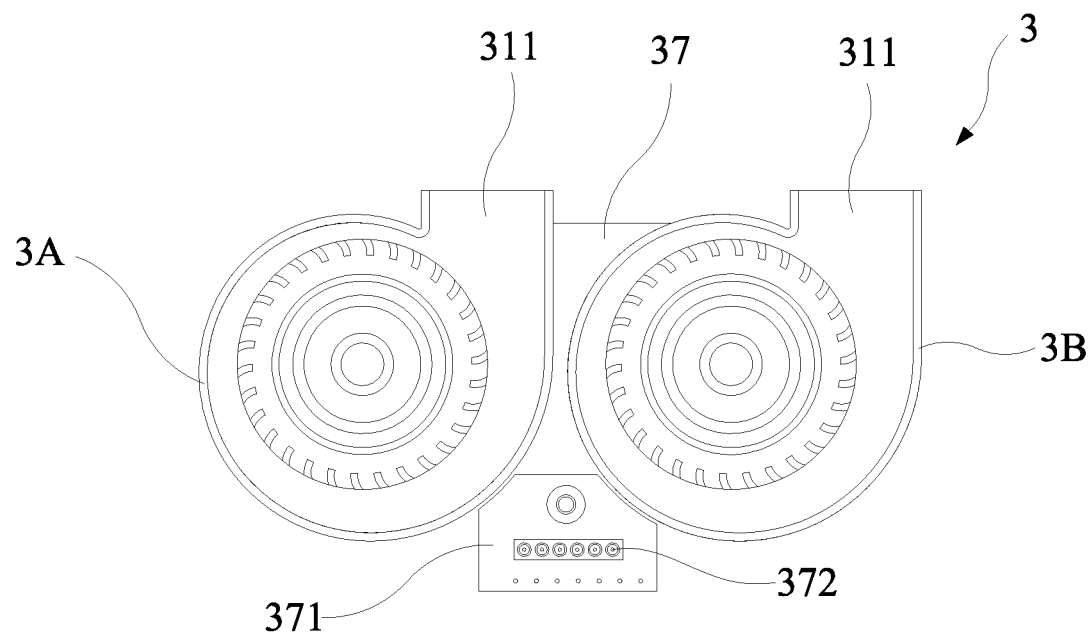
FIG. 13 is a top view of a second embodiment of the fan of the present invention.
Figure 14:
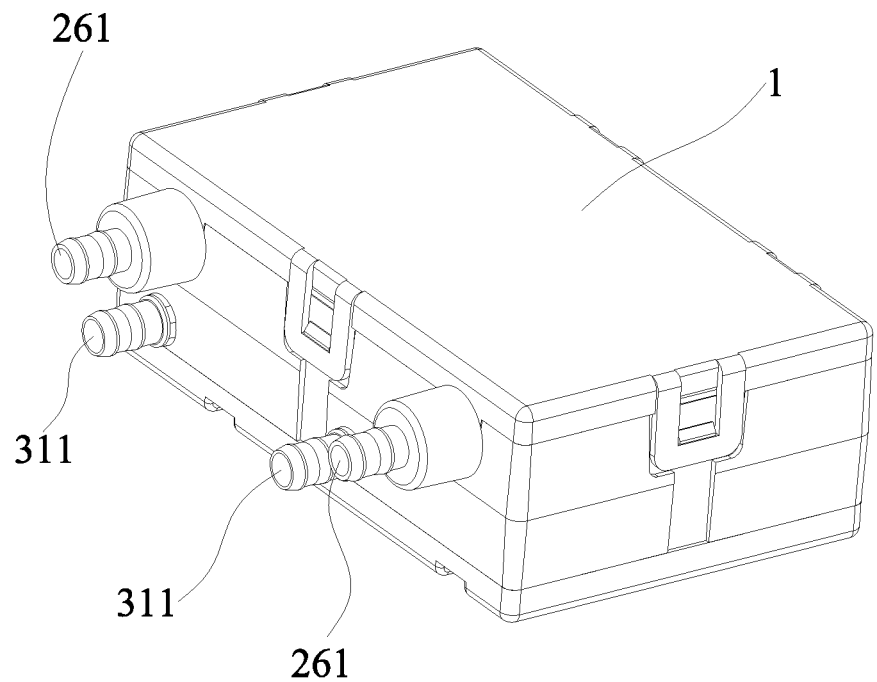
FIG. 14 is a perspective view of the present invention provided with the fan of FIG. 13.

As shown in FIG. 11 to FIG. 17, the air outlet ends 311 of the first and second fans 3A, 3B of the present invention may have various arrangement modes. FIG. 11 illustrates a first embodiment of the first and second fans 3A, 3B. As shown in the figure, the air outlet ends 311 of the first and second fans 3A, 3B may be disposed at two sides of the housing 1. FIG. 13 and FIG. 14 illustrate a second embodiment of the first and second fans 3A, 3B. The air outlet ends 311 of the first and second fans 3A, 3B may be disposed at the same side of the housing 1. FIG. 17 illustrates a third embodiment of the first and second fans 3A, 3B. The air outlet ends 311 of the first and second fans 3A, 3B may be disposed at adjacent sides of the housing 1.

Figure 15:
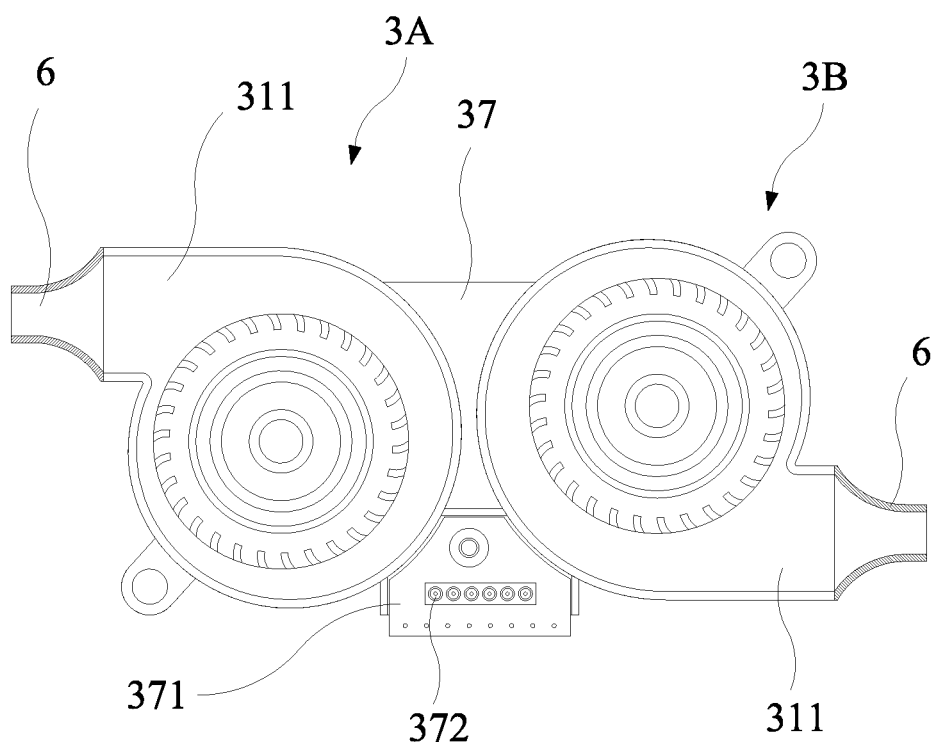
FIG. 15 is a schematic view of the fan, as shown in FIG. 11, connected with the noise reduction connector.
Figure 16:
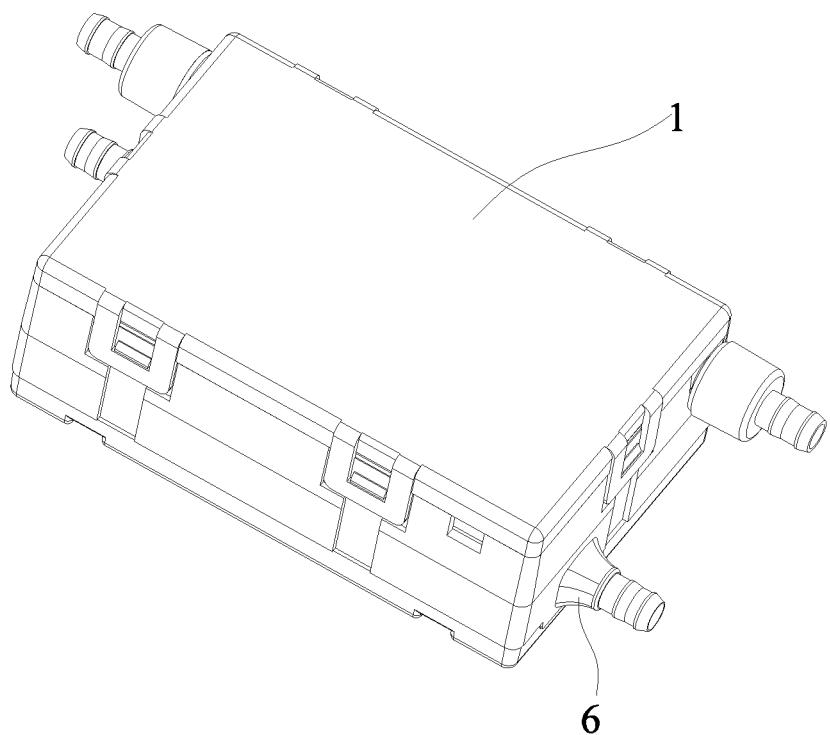
FIG. 16 is a perspective view of the present invention provided with the fan of FIG. 15.

Furthermore, as shown in FIG. 15 and FIG. 17, each of the air outlet ends 311 of the first fan 3A and the second fan 3B is provided with a noise reduction connector 6 having a smooth an inner wall. The noise reduction connector 6 is tapered outwardly from the air outlet ends 311 of the first fan 3A and the second fan 3B. Experimentally, when the first fan 3A and the second fan 3B are not provided with the noise reduction connector 6, the flow rate is 3.1 L/min and the reflux rate at the flow outlet is 33%. After adding the noise reduction connector 6, the flow rate is 3.2 L/min and the reflux rate at the flow outlet is 1.2%. Thus, after the noise reduction connector 6 is added, the suction of the first fan 3A and the second fan 3B obviously increases, and the noise can be significantly reduced.

Figure 18:
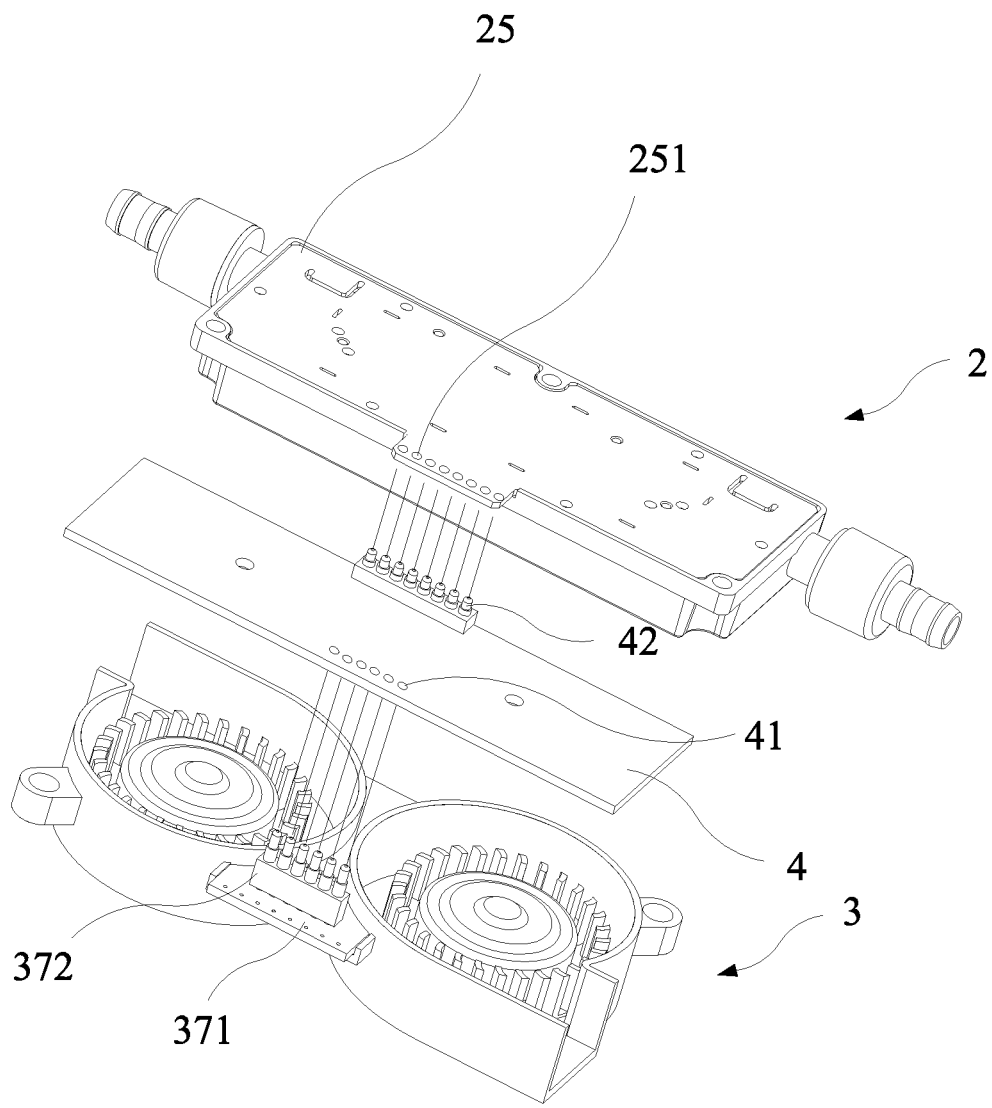
FIG. 18 is an exploded view of the air quality detection module, the main control PCB and the fan of the present invention.
Figure 19:
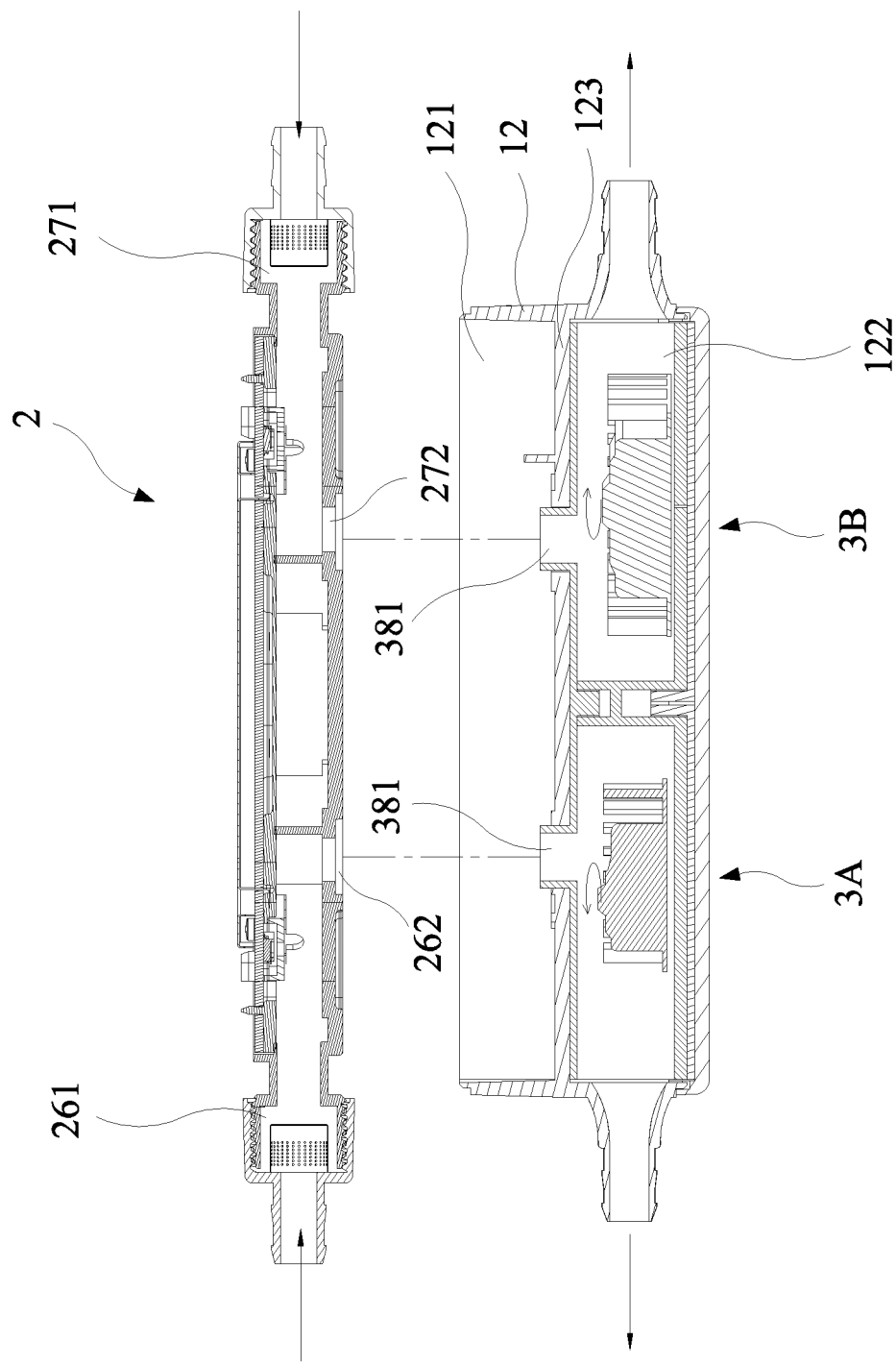
FIG. 19 is an exploded sectional view of the fan and the air quality detection module of the present invention.

As shown in FIG. 1 in conjunction with FIG. 18 and FIG. 19, in order to facilitate the fully automated assembly of the dual-passage air quality detection device of the present invention, the fan of the present invention no longer uses lead terminals, but integrates the circuit directly on the thimble connector 371. The thimbles 372 on the thimble connector 371 are directly aligned and connected with the main control PCB 4. The main control PCB 4 is provided with a plurality of conductive contacts 41 corresponding to the thimbles 372 and a plurality of pins 42 corresponding to the metal contacts 251 of the air quality detection module 2. When assembled, the main control PCB 4 is mounted on the middle casing 12, the air quality detection module 2 is mounted in the upper chamber 121 of the middle casing 12, and the fan 3 is mounted in the lower chamber 122 of the middle casing 12. The thimbles 372 of the thimble connector 371 of the fan 3 are connected with the conductive contacts 41 of the main control PCB 4. The metal contacts 251 of the circuit board 25 of the air quality detection module 2 are connected with the pins 42 of the main control PCB 4.

For detecting the air quality, one of the passages is communicated with the inside of the vehicle, and the other of the passages is communicated with the outside of the vehicle to form two independent air passages for detection. Each of the passages corresponds to one fan 3 for independent sampling, not affecting each other. The air is exhausted through the fan 3. The laser light emitted from the laser module 22 passes through the air passage. The scattered light of dust particles in the air passage is fed back to the photodiode. The potential of the photodiode changes by circuit data processing to obtain the PM2.5 value.

Figure 20:
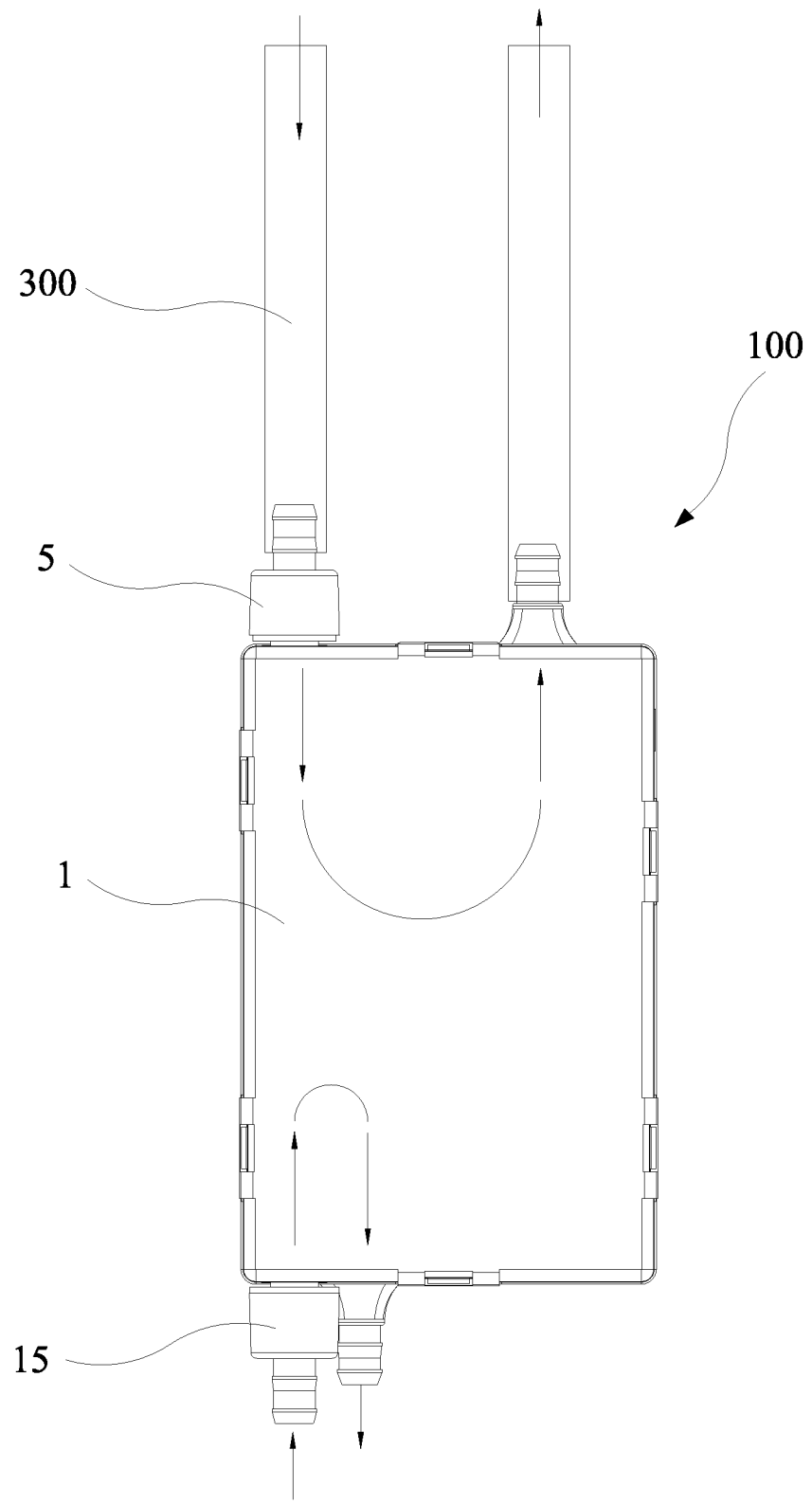
FIG. 20 is a schematic view showing the operation of the present invention.

As shown in FIG. 20, the dual-passage air quality detection device of the present invention is provided with the two fans 3. The two fans 3 respectively sample the air inside and outside the vehicle and do not influence each other so as to effectively reduce the influence on the sampling airflow of the module and to ensure the accuracy of detection when the air conditioner is turned on. Moreover, in the present invention, the transmitting ends of the two laser modules 22 are arranged in a V-shaped configuration, which not only effectively reduces the longitudinal length of the air detection module but also reduces the overall size of the product.

Secondly, the present invention can meet the requirements of the fully automated assembly. The thimbles 372 of the thimble connector 371 of the fan 3 are connected with the conductive contacts 41 of the main control PCB 4, and the metal contacts 251 of the circuit board 25 of the air quality detection module 2 are connected with the pins 42 of the main control PCB 4, thereby improving the production and assembly efficiency greatly and facilitating inspection and maintenance.

In addition, the air outlet ends of the first fan 3A and the second fan 3B of the present invention are connected with the noise reduction connectors 6 to provide great suction and to lower the noise, which improves the user's experience. The upper portion of the fan casing 31 is covered with the fan sealing cover 38, and the upper portion of the fan casing 31 is provided with the fan cushion 39 to effectively reduce the noise when the first fan 3A and the second fan 3B are running.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. A dual-passage air quality detection device, comprising a housing, an air quality detection module, a fan and a main control PCB (printed circuit board) connected with the air quality detection module and the fan being provided in the housing; the air quality detection module being formed with a first passage and a second passage therein, the first passage and the second passage having sampling openings and air outlets respectively, characterized by: the fan including a first fan and a second fan corresponding to the first passage and the second passage, an air inlet end of the first fan being connected with the air outlet of the first passage, an air inlet end of the second fan being connected with the air outlet of the second passage, air outlet ends of the first and second fans being communicated with external air, the air quality detection module including a first laser module and a second laser module corresponding to the first passage and the second passage, transmitting ends of the first and two laser modules being arranged in a V-shaped configuration, the transmitting end of the first laser module being located in the first passage, a first photodiode being provided in the first passage, facing the transmitting end of the first laser module, the transmitting end of the second laser module being located in the second passage, a second photodiode being provided in the second passage, facing the transmitting end of the second laser module, the first and second laser modules and the first and second photodiodes being electrically connected to a circuit board of the air quality detection module, the circuit board being electrically connected to the main control PCB.

2. The dual-passage air quality detection device as claimed in claim 1, wherein the air quality detection module has a rectangular main body and the circuit board, and the first passage, the second passage, the first and second laser modules and the first and second photodiodes are disposed in the main body.

3. The dual-passage air quality detection device as claimed in claim 2, wherein the sampling openings of the first passage and the second passage are disposed at a same side of the main body, the first passage and the second passage are respectively L-shaped or J-shaped, and the transmitting ends of the first laser module and the second laser module face respective corners of the L-shaped or J-shaped first and second passages.

4. The dual-passage air quality detection device as claimed in claim 2, wherein the sampling openings of the first passage and the second passage are disposed at two sides of the main body respectively, the first passage and the second passage are respectively Z-shaped, and the transmitting ends of the first laser module and the second laser module face respective corners of the Z-shaped first and second passages far away from the sampling openings.

5. The dual-passage air quality detection device as claimed in claim 1, wherein each of the sampling openings of the first passage and the second passage is connected to a sampling tube through a connector, one end of the connector is connected to the sampling openings, another end of the connector is connected to the sampling tube, the connector has an accommodation chamber therein, the accommodation chamber is provided with a filter cartridge, the filter cartridge is provided with a plurality of air holes for air circulation, and the accommodation chamber is provided with a water tank under the air holes for storing condensate water.

6. The dual-passage air quality detection device as claimed in claim 5, wherein the connector includes a plug connected with the sampling openings and a tube plug connected with the sampling tube, the plug is connected to the tube plug, the junction of the plug and the tube plug is formed with the accommodation chamber, the filter cartridge is disposed in the accommodation chamber, one end of the filter cartridge, connected with the tube plug, is formed with the air holes, the filter cartridge is directly formed with the water tank below the air holes, and a sealing gasket is provided in the accommodation chamber at the end where the filter cartridge is connected to the tube plug.

7. The dual-passage air quality detection device as claimed in claim 5, wherein the connector includes a plug connected with the sampling openings and a tube plug connected with the sampling tube, the plug is connected to the tube plug, one end of the tube plug is connected to the sampling pipe, another end of the tube plug is connected to the plug, the accommodation chamber is disposed between the two ends of the tube plug, the end of the tube plug, connected with the plug, extends into the accommodation chamber and is formed with a protruding wall so that the accommodation chamber is formed with the water tank around the protruding wall, the filter cartridge has an arc shape and is disposed between the protruding wall of the tube plug and the plug, and a sealing gasket is provided between the filter cartridge and the protruding wall of the tube plug.

8. The dual-passage air quality detection device as claimed in claim 2, wherein the first fan and the second fan each include a fan casing, the fan casing is provided with a rotor and a wind wheel therein, the fan casings of the first and second fans are connected together by a connecting plate, the connecting plate is provided with a thimble connector thereon, the rotor is provided with a plurality of leads, each of the leads is connected to the thimble connector, the thimble connector is provided with a plurality of thimbles thereon, the main control PCB is provided with a plurality of conductive contacts corresponding to the thimbles, the circuit board of the air quality detection module is provided with a plurality of metal contacts, and the main control PCB is provided with a plurality of pins corresponding to the metal contacts.

9. The dual-passage air quality detection device as claimed in claim 8, wherein a fan sealing cover is provided to mate with a top of the fan casing, the fan sealing cover has connection holes corresponding in position to the first fan and the second fan respectively, and a fan cushion is provided at a bottom of the fan casing.

10. The dual-passage air quality detection device as claimed in claim 1, wherein each of the air outlet ends of the first fan and the second fan is provided with a noise reduction connector having a smooth an inner wall, and the noise reduction connector is tapered outwardly from the air outlet ends of the first fan and the second fan.

11. The dual-passage air quality detection device as claimed in claim 1, wherein the housing includes an upper casing, a middle casing and a lower casing, the upper casing is mated with an upper portion of the middle casing, the lower casing is mated with a lower portion of the middle casing, the middle casing is partitioned into an upper chamber and a lower chamber by a partition, the air quality detection module is disposed in the upper chamber of the middle casing, the first fan and the second fan are disposed in the lower chamber of the middle casing, the main control PCB is disposed in the upper chamber or the lower chamber of the middle casing, the partition has two through holes corresponding to the first passage and the second passage, and the partition further has perforations for the main control PCB to connect with the first and second fans or the air quality detection module.

\* \* \* \* \*